(12) United States Patent
Vrijens et al.

(10) Patent No.: US 6,822,554 B2
(45) Date of Patent: Nov. 23, 2004

(54) SYSTEMS AND METHODS FOR MEDICATION MONITORING

(75) Inventors: Bernard Vrijens, Eben-Emael (BE); John Urquhart, Palo Alto, CA (US); Erik De Klerk, Kerkrade (NL); Jean-Michel Metry, Sion (CH)

(73) Assignee: Hexalog SA (CH)

( * ) Notice: Subject to any disclaimer, the term of this patent is extended or adjusted under 35 U.S.C. 154(b) by 66 days.

(21) Appl. No.: 10/342,655

(22) Filed: Jan. 13, 2003

(65) Prior Publication Data

US 2003/0135392 A1 Jul. 17, 2003

Related U.S. Application Data

(60) Provisional application No. 60/348,578, filed on Jan. 11, 2002.

(51) Int. Cl.[7] .................................................. G08B 1/00
(52) U.S. Cl. ........................ 340/309.16; 340/3.1; 221/2; 221/8; 706/924; 368/1
(58) Field of Search ...................... 340/309.16, 309.15, 340/309.4, 531, 534, 539.12, 3.1, 3.3, 3.31, 3.32, 3.34; 706/924; 368/1, 10; 128/920, 923; 177/25.19; 221/2, 8

(56) References Cited

U.S. PATENT DOCUMENTS

| | | |
|---|---|---|
| 4,616,316 A | 10/1986 | Hanpeter et al. |
| 4,682,299 A | 7/1987 | McIntosh et al. |
| 4,831,562 A | 5/1989 | McIntosh et al. |
| 4,837,719 A | 6/1989 | McIntosh et al. |
| 4,899,839 A | 2/1990 | Dessertine et al. |
| 4,911,327 A | 3/1990 | Shepherd et al. |
| 4,926,572 A | 5/1990 | Holmes |
| 4,939,705 A | 7/1990 | Hamilton et al. |
| 4,942,544 A | 7/1990 | McIntosh et al. |
| 4,962,491 A | 10/1990 | Schaeffer |
| 4,970,669 A | 11/1990 | McIntosh et al. |
| 4,971,221 A | 11/1990 | Urquhart et al. |
| 5,014,798 A | 5/1991 | Glynn |
| 5,016,172 A | 5/1991 | Dessertine |
| 5,954,641 A * | 9/1999 | Kehr et al. .................. 600/300 |

OTHER PUBLICATIONS

Vrijens, B., Dose–timing Information Improves the Clinical Explanatory Power of Data on Patient Compliance with Antiretroviral Drug Regimens, Poster from Society for Risk Analysis, New Orleans, Louisiana, Dec. 9, 2002.

Vrijens, B., et al., Dose Timing Information Improves the Clinical Explanatory Power of Data on Patient Compliance with Antiretroviral Drug Regimens, Poster for Apr. 25–27, 2002 LACDR Meeting in Noordwijkerhout, Netherlands.

Vrijens, B., Dose–Timing Information Improves the Clinical Explanatory Power of Data on Patient Compliance with Antiretroviral Drug Regimens, Abstract for Apr. 25–27, 2002 LACDR Meeting in Noordwijkerhout, Netherlands.

* cited by examiner

Primary Examiner—Jeffery Hofsass
Assistant Examiner—Jennifer Stone
(74) Attorney, Agent, or Firm—Foley & Lardner LLP

(57) ABSTRACT

The present invention relates to a method and system of medication monitoring which includes analyzing data on the clinical consequences of variable patient compliance with prescribed drug regimens, communicating to caregivers and/or patients the compliance-dependent probabilities of two clinically important transitions in health status: substantive improvement in the patient's health status and substantive deterioration in the patient's health status, defining acceptable levels of the respective probabilities of deterioration and of improvement, and intervening when appropriate to improve the patient's compliance, in order to achieve mutually-agreed upon maintenance, improvement, or avoidance of deterioration in health status.

23 Claims, 1 Drawing Sheet

SYSTEMS AND METHODS FOR MEDICATION MONITORING

CROSS-REFERENCE TO RELATED APPLICATIONS

Figure 1:
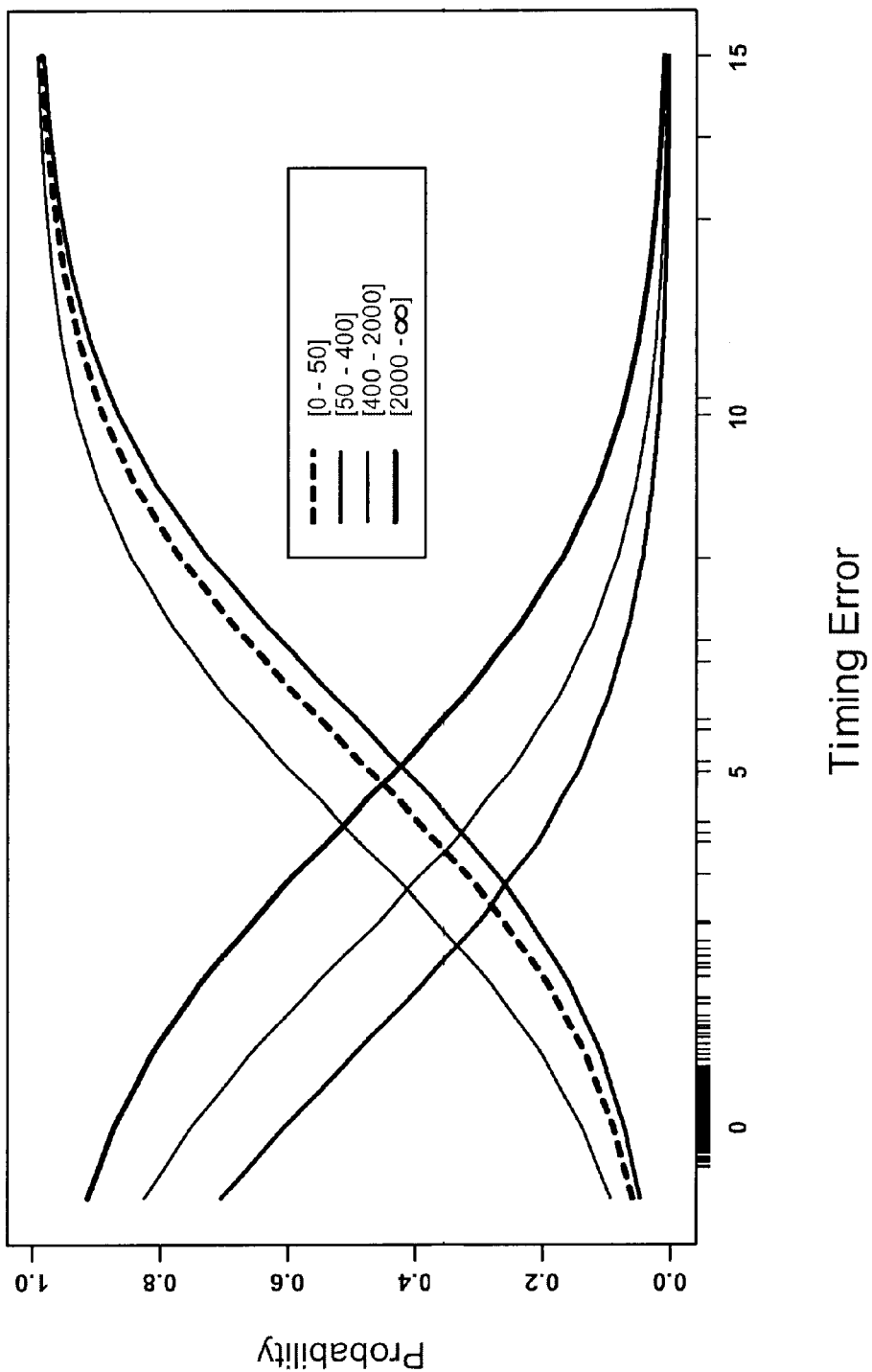

This application claims priority to U.S. Provisional Application Ser. No. 60/348,578, filed Jan. 11, 2002, which is incorporated herein by reference in its entirety.

FIELD OF THE INVENTION

The invention relates to a system and method of monitoring patient compliance with a prescribed drug regimen and warning or prompting the patient based on calculated probabilities of improvement or deterioration of the patient's health.

BACKGROUND OF THE INVENTION

It is now well-established, and well-known to those skilled in the art, that electronic medication event monitoring, also known in the medical literature as MEMS® Monitoring, is the best available method of measuring and compiling the drug dosing histories of ambulatory patients (1–4). Medication dispensers which monitor deviations from a prescribed dosing regimen are described in U.S. Pat. Nos. 4,725,997 and 4,748,600 which are incorporated herein by reference in their entirety.

It is also well-established in the medical literature, and well-known to those skilled in the art, that the actions of prescription drugs depend upon the amount (dose) of drug taken and the time-intervals that separate successive doses of drug. The specifics of the dose- and time-dependent actions of drugs vary, not only from one drug to another, but within the same drug, depending upon how it is formulated (5). Thus, each pharmaceutical product in use poses the question of how best to define its dynamic relations between the history of its dosing and the clinical consequences attributable to the drug's dose- and time-dependent actions. A variety of methods exist to ascertain these dynamic relations, but their applications are in some instances limited by ethical constraints on experimentation with humans and/or by limitations in one's ability to measure appropriate clinical variables. In general, however, one seeks the most robust dynamic model for projecting the clinical effects of the patient's variable exposure to the drug, wherein 'exposure' means not only the quantity of drug ingested, but also the time-intervals separating individual doses.

REFERENCES

The following publications are cited in parenthesis in this application. All of the following references are herein incorporated by reference in their entirety to the same extent as if each individual reference was specifically and individually indicated to be incorporated herein by reference in its entirety.

1. Liu H, Golin C E, Miller L G, Hays R D, Beck C K, Sanandaij S, Christian J, Maldonado T, Duran D, Kaplan A, Wenger N S. A comparison study of multiple measures of adherence to HIV protease inhibitors. Ann Inter Med 2001; 134:968–77.

2. Arnsten J, Demas P, Farzadegan H, Grant R, Gourevitch M, Chang C, Buono D, Eckholt H, Howard A, Schoenbaum E. Antiretroviral therapy adherence and viral suppression in HIV-infected drug users: comparison of self-report and electronic monitoring. Clinical Infectious Diseases 2001; 33:1417–23.

3. Cramer J A. Microelectronic system for monitoring and enhancing patient compliance with medication regimens. Drugs 49:321–7, 1995.

4. Urquhart J, de Klerk E. Contending paradigms for the interpretation of data on patient compliance with therapeutic drug regimens. Stat Med 17:251–267, 1998.

5. Urquhart J. Controlled drug delivery: pharmacologic and therapeutic aspects. J Internal Med 248:357–76, 2000.

6. Paterson D L, Swindells S, Mohr J, Brester M, Vergis E N, Squier C, Wagener M M, Singh N. Adherence to protease inhibitor therapy and outcomes in patients with HIV infection. Ann Int Med 133:21–30, 2000.

7. Gross R, Friedman H M, Bilker W B, Strom B L. Adherence to nelfinavir: magnitude and patterns associated with HIV suppression. Poster presentation at the $40^{th}$ Interscience Conference on Antimicrobial Agents and Chemotherapy, Toronto, Canada, Poster 790, Sept 17–20, 2000.

8. Urquhart J. Ascertaining how much compliance is enough with outpatient antibiotic regimens. Postgrad Med J 68 (suppl 3): S49–59, 1992.

9. U.S. Pat. No. 4,725,997 to Urquhart J. and Elgie H. assigned to APREX Corp.

10. U.S. Pat. No. 4,748,600 to Urquhart J. assigned to APREX Corp.

11. Turner B J, Hecht F M. Improving on a coin toss to predict adherence to medications. Ann Int Med 134:1004–6, 2001.

SUMMARY OF THE INVENTION

The present invention relates to a method and system of medication monitoring which includes analyzing data on the clinical consequences of variable patient compliance with prescribed drug regimens, communicating to caregivers and/or patients the compliance-dependent probabilities of two clinically important transitions in health status: substantive improvement in the patient's health status and substantive deterioration in the patient's health status, defining acceptable levels of the respective probabilities of deterioration and of improvement, and intervening when appropriate to improve the patient's compliance, in order to achieve mutually-agreed upon maintenance, improvement, or avoidance of deterioration in health status.

In accordance with one aspect of the present invention, a method of medication monitoring includes the steps of analyzing data on the clinical consequences of variable patient compliance with a prescribed drug regimen to determine the compliance-dependent probabilities of (i) substantive improvement in the patient's health status, and (ii) substantive deterioration in the patient's health status, communicating the compliance-dependent probabilities to caregivers and patients, defining acceptable levels of the probabilities of improvement and deterioration, prescribing a drug regimen for the patient, measuring patient compliance with the prescribed drug regimen with a medication dispenser having a recorder for recording dosing events, and intervening with the patient to improve compliance with an intensity and urgency based on the defined acceptable levels of probabilities.

In accordance with another aspect of the present invention, a method of medication monitoring includes the steps of identifying a patient with a condition treatable with a prescribed drug regimen, prescribing a drug regimen for the patient, defining an acceptable level of compliance with the prescribed drug regimen, based on an analysis of clinical compliance data involving the calculation of a parameter, referred to as cubic distance or Timing Error, from the variations in intervals between dosages, monitoring compliance of the patient with the prescribed drug regimen with a medication dispenser having a recorder for recording dosing events, and warning the patient with a graduated warning system that is based on the defined acceptable level of compliance.

In accordance with a further aspect of the present invention, a method of medication monitoring includes the steps of analyzing data on the clinical consequences of variable patient compliance with a prescribed drug regimen, to determine the compliance-dependent probabilities of (i) substantive improvement in the patient's health status, and (ii) substantive deterioration in the patient's health status, defining patient acceptable levels of the probabilities of improvement and deterioration, measuring patient compliance with the prescribed drug regimen with a medication dispenser having a recorder for recording dosing events, and intervening with the patient to improve compliance when the defined acceptable levels of probabilities are exceeded.

In accordance with an additional aspect of the present invention, a system for medication monitoring includes a computer-readable medium containing executable code, and a medication dispenser having a recorder for recording dosing events, and a warning system for warning the patient of non-compliance with an intensity and urgency based on a defined acceptable levels of probabilities of treatment-dependent change in health status. The executable code is provided for analyzing data on the clinical consequences of variable patient compliance with a prescribed drug regimen to determine the compliance-dependent probabilities of (i) substantive improvement in the patient's health status, and (ii) substantive deterioration in the patient's health status, and communicating the compliance-dependent probabilities to caregivers and patients.

BRIEF DESCRIPTION OF THE DRAWING FIGURES

FIG. 1 is a graph of the association between Timing Error and respective probability to improve/deteriorate in viral load.

DETAILED DESCRIPTION OF THE PREFERRED EMBODIMENTS

The method and system of the present invention are generally based on novel methods including steps of analyzing data on the clinical consequences of variable patient compliance with prescribed drug regimens, developing means of communicating to both caregivers and patients the compliance-dependent probabilities of two clinically important transitions in health status: substantive improvement in the patient's health status and substantive deterioration in the patient's health status, and defining acceptable levels of the separate probabilities of deterioration and of improvement. The probable costs of intervening to improve the patient's compliance can then be projected from the patient's present level of compliance with prescribed drug regimens, in order to achieve and maintain a mutually-agreed upon health status, to achieve improvement in health status, and to avoid deterioration in health status.

A management system is associated with the method, guided by ongoing measurements of the patient's compliance with the prescribed drug regimen(s). An integral part of the management system involves the triggering of specific interventions to improve compliance, with an intensity and urgency that is based on estimated probabilities of substantive improvement and of substantive deterioration in the patient's health status, as derived from the patient's current level of compliance.

The systems and methods described herein are used primarily for doing business in the healthcare arena for treatment of patients, but may also be used in other arenas including the management and communication of actuarial risk, based on, e.g., the projected impact of improvements or deteriorations in recognized actuarial risk factors, such as blood pressure, body weight or related indices of body size, plasma levels of cholesterol and its various fractions, parameters of diabetes control, including glycosylated hemoglobin levels or glucose concentrations in blood; other biochemical or biophysical indicators of progression of disease.

The present invention will be described with reference to an example of HIV (human immunodeficiency virus) infected patients and the use of drugs of the anti-retroviral (ARV) class used to treat HIV infection. The thesis entitled "Analyzing time-varying patters of human exposure to xenobiotics and their biomedical impact" by Bernard Vrijens (Vrijens thesis) is incorporated hereby reference in its entirety. The Vrijens thesis discusses in detail the analysis of clinical data on the clinical consequences of variable patient compliance with a prescribed ARV drug regimen to determine the compliance-dependent probabilities of (i) substantive improvement in the patient's health status (i.e. reduction in viral load), and (ii) substantive deterioration in the patient's health status (i.e. increase in viral load).

Although the present invention will be described with reference to the HIV example, it should be understood that the methods and systems of the present invention may also be applied to the treatment of patients with a wide variety of known prescription drugs for a wide variety of human diseases.

The Vrijens thesis describes that patient compliance (the extent to which the patients' recorded dosing history corresponds to the prescribed regimen of drug administration) for protease inhibitors in dose-timing of protease inhibitors in losing virologic control has been suggested as a key factor. The thesis looks directly at the explanatory power of variations in interdose intervals on the success and failure of anti-retroviral drug therapy.

In summary, the Vrijens thesis discusses the analysis of clinical data on patient compliance with a prescribed ARV drug regimen. The Vrijens analysis divides patients into four strata of viral loads (0–50, 50–400, 400–2000, and 2000+ copies/ml). Substantive improvement in the patient's health status occurs when the patient's viral load moves to a lower strata, while substantive deterioration in the patient's health status occurs when the patient's viral load moves to a higher strata. From electronically compiled dosing histories of naïve patients taking various protease inhibitors the parameters of patient compliance were derived including percentage of prescribed doses taken (taking compliance), percentage of treatment days during which the correct number of doses were taken (correct dosing) and percentage of interdose-intervals within 25% of prescribed interdose-intervals (timing compliance).

A new parameter, Timing Error, was also derived, which is related to the 3rd moment of the distribution of interdose intervals.

The Timing Error is calculated by the formula:

$$CD_i = \sqrt[3]{\frac{1}{n_i}\sum_k (\delta_{ik}^* - \delta_0)^3}$$

where:

$CD_i$ is the Timing Error (or cubic distance) for the patient i, $n_i$ is the number of dosing intervals observed for the patient i, $\delta^*_{ik}$ is the kth observed dosing interval for the ith patient (k=1, ..., $n_i$); and $\delta_0$ is the prescribed dosing interval (i.e. 24 hours for a once a day medication and 12 hours for a twice a day medication).

Compared with other, standard measures of drug exposure, the Timing Error has a greater explanatory power than any of the standard parameters of patient adherence or drug exposure for the separate probabilities of improvement and deterioration in the patient's viral load, which is the widely accepted surrogate marker for clinical status in the preferred embodiment, namely HIV infection.

A model that predicts changes from one category of viral load to a lower one (improvement) or higher (deterioration) showed that Timing Error is a superior predictor of changes in viral load, compared to analyses based on the usual parameters of patient compliance. This result suggests that a few substantially prolonged inter-dose intervals have greater impact on viral load than many marginally prolonged inter-dose intervals, a factor not considered in conventional compliance analysis. Plots of Timing Error on the probabilities of change in viral load differ among protease inhibitors, suggesting that drugs of this class have differing degrees of forgiveness for longer interdose intervals.

The calculation of Timing Error allows the data to be appropriately weighted so that longer periods between doses are more heavily weighted than several smaller such periods. For example, if in a 30 day period of observation a patient is late in taking a dose 30 times, each in the amount of 1 hour, the resulting cumulative gap in the drug's antiviral action of 30 hours is less likely to have adverse affects on the patient's health than if the patient were twice late by 15 hours in taking the next scheduled dose, for the same cumulative gap of 30 hours in antiviral drug action. Thus, even if the total amount of the delays in dosing are identical, the clinical results are likely to differ. To address this difference, a useful indicator in determining the probabilities of improvement or deterioration has been found to be the parameter called "cubic distance" or "Timing Error" described above, which is computed from the variations in intervals between dosages. Timing Error puts most emphasis on the longer lapses in dosing, and less emphasis on the shorter lapses, which are usually more frequent, but are less likely to have clinical impact, except with unusually short-acting drugs that lose their clinical effect from only minor lapses in dosing.

Dose-timing data increase the explanatory power of data on patient compliance for antiretroviral treatment outcomes. The results suggest that avoidance of long interdose intervals should be a priority in efforts to improve patient compliance. The explanatory power of dose-timing data will likely vary from one drug and treatment situation to another.

FIG. 1 shows a graph of the probability of improvement (sloping downward from left to right) and the probability of deterioration (sloping upward from left to right) versus the cubic distance (Timing Error), computed from the variations in interdose intervals. The use of these drug-specific data allows the caregiver and the patient to set mutually acceptable probability levels respectively for improvement and deterioration particular to the patient and the drug in question. As will be described in further detail below, the caregiver and patient may then establish a warning system, individualized for the patient, the drug, and the patient's choice of acceptable risk levels for improvement and deterioration. The warning system may include a medication dispenser having a recorder for recording dosing events, a communication device for communicating dose-timing data to a remote location and/or other warning techniques. The different warning systems employed will have different costs associated therewith, and these costs can be taken into account in setting the patient's probability levels.

Internal Exposure

A useful construct, proposed in this application, is the patient's internal exposure to the drug, which is a model-based projection derived from the electronically recorded dosing history and pre-existing knowledge of the drug's pharmacokinetic parameters. The computation of internal exposure allows one to estimate when the concentration of antiviral drug in plasma drops below the so-called EC50, which is the commonly agreed-upon minimum concentration of drug in plasma for therapeutic effectiveness. The utility and limitations of internal exposure are described in the Vrijens article, which is incorporated in its entirety in this application.

Separate Probabilities for Improvement and for Deterioration

It is altogether novel, and unobvious to those skilled in the art, that the compliance-dependent probability of change in the patient's current health status will have different values, depending upon whether the change is for the better, or for the worse. In other words, the dosing requirements for preventing worsening of a disease may differ appreciably from the dosing requirements for improvement. Estimating those different values is a primary objective of a satisfactorily robust model for projecting the clinical effects of the patient's variable exposure to the drug, created by the patient's variable compliance with the prescribed drug regimen. Many medical researchers have written about the impact of variable compliance with prescribed drug regimens, but all have done so in terms of projecting the patient's unidirectional trajectory in disease severity. For example, Paterson et al. (6) have published a relationship between percentage of prescribed doses taken and 'virological failure', defined as the failure of the viral load in plasma to fall during a course of treatment with drugs of the class known as protease inhibitors. Likewise, Gross and his colleagues (7) describe their work in terms of the failure of viral load in plasma to fall during a course of treatment with protease inhibitors. So also did Liu et al. (1) and Arnsten et al. (2). Indeed, Liu et al. (1) were taken to task in an editorial accompanying their paper (11) for neglecting to use information on dose timing in their analysis, though the two editorialists offered no suggestions for how, specifically, to do so.

In earlier published work, Urquhart (8) re-analyzed the classical studies of Wood, Feinstein and others on the compliance-dependent prevention of recurrent acute rheumatic fever, writing strictly in terms of impact of the estimated aggregate drug intake on the likelihood of failed preventive treatment.

Statistical Complexity Notwithstanding, A Simple Foundation for Risk Communication Another aspect of the present application is the foundation that it lays for simplified means of communicating to both caregivers and patients the probabilistic impact of a presently maintained level of compliance with prescribed drug regimens on the prospects for improvement, on the one hand, or deterioration, on the other hand, in health status. These means of communication are also able to show both caregivers and patients the probabilistic impact of potential increases or decreases in patient compliance with the prescribed drug regimens on the separate prospects of clinically substantive improvement or deterioration in health status.

With simplified means for communicating risk information comes better-informed clinical decision-making, based on informed cooperation between caregivers and patients. These means of communicating risk information and engaging the patient in informed decision making is a means for patient empowerment.

Capability of Projecting Cost Implications of Risk Level Choices

Naturally, interventions to effect change, and urgent interventions to prevent harmful lapses in dosing, are not without their costs in professional time that has to be devoted to the treatment program, and the monetary costs associated therewith. These interventions also impact the patient, as they may occur inconveniently frequently. In general, the higher one sets the goals for improvement and the lower one sets the risk-threshold for deterioration, the more frequent will occur these interventions, and the greater their costs will be.

Accordingly, yet another aspect of the present application is the ability to project, or simulate, the economic and management consequences, for both health professionals and the patient, of setting a particular levels of acceptable probabilities of improvement and of deterioration, given the patient'prevailing level of compliance with the prescribed drug regimens.

Color-coded Management System: Ultimate Simplicity

Still yet another aspect of the present application is a management system based on the use of color-coded warning conditions that trigger color-specific actions to terminate a lapse in dosing, to initiate a special interim regimen of dosing designed to reduce risk of adverse outcome, and to improve compliance.

According to one embodiment of the invention, color-coded warnings include green-zone, yellow-zone, red-zone, and flashing red-zone to indicate increasing severity of continued lapse in dosing. These color-coded warnings may be made to the patient by way of lights, sounds, or other warnings on a dosing device. The warnings may, alternatively, be made to the caregiver or another type of health care professional by way of automatic or semi-automatic communication between electronics associated with a dosing device or medication dispenser and a remote center or caregiver's office, from which apt instructions may be sent to the patient by one or more available means, e.g., regular or wireless telephone, fax, computer, television or other.

For example, a medication dispenser may be provided with electronics which automatically communicate, e.g. via cellular telephone, with the remote warning center or caregiver's office each time a prescribed warning condition (red warning) is reached. Alternatively, the dosing history may be downloaded periodically from the medication dispenser to a personal computer and transmitted by the personal computer to the remote warning center or caregiver's office. As discussed above, the many different methods of providing warnings to the patient and/or caregiver carry different costs which may be taken into account in selecting a particular warning system and warning level for the patient.

The transitions between the colors are dictated by changing levels of risk of deterioration or of chance for improvement, depending upon which is the main focus at a given time in a given patient's health status.

Comparative Locations of Probability Curves Reveal Competitive Advantages in Forgiveness It will be obvious to those skilled in the art that the set of probabilities, as exemplified by FIG. 1, will differ for different drugs in their shape and location on the 2-dimensional plot of probability versus the 'cubic distance' (Timing Error). For example, drugs that are more 'forgiving' of occasional lapses in dosing than others will have maintain a low probability of deterioration out to a higher magnitude of cubic distance (Timing Error) than will drugs that are less 'forgiving'. Analogously, the more forgiving of two drugs will maintain a higher level of probability of improvement out to a higher cubic distance (Timing Error) than will the less forgiving of the two drugs. These differences will translate into simpler, less intrusive, less time-intensive, less costly treatment regimens for a given level of patient compliance with more forgiving drugs than with less forgiving drugs. Forgiveness is formally defined as the post-dose duration of effective drug action minus the recommended interval between doses (4). It will be obvious to those skilled in pharmaceutical marketing that the ability to communicate both medical and economic superiority of one pharmaceutical versus another gives marketing advantage to the product with the superior medical and economic claims.

The method of the present invention can recognize situations in which very meticulously punctual dosing is necessary for improvement, while the patient can maintain the status quo and not get worse by maintaining a much less strictly punctual dosing record. One can foresee circumstances in which a patient dosing schedule can be relaxed during a time of disruption of lifestyle, such as traveling and the status quo maintained; later, the schedule can then be made more strict at other times to make a substantial push for improvement in condition.

Forging Simplicity from Complexity

Finally, the method of computing exposure-dependent probabilities of improvement and of deterioration will appear arcane and difficult for most health professionals and almost all patients to grasp and communicate effectively. Part of the novel method of doing business is the translation of results of advanced statistical calculations into simple terms that will allow caregivers and patients to see reliable estimates of the costs, in money and time, of setting, e.g., a 10% probability of deterioration and an 80% probability of improvement, versus other choices, e.g., 5% and 90%, 2% and 95%, and so forth. Each of these choices of probability-pairs has its respective implications for the frequency with which the 'green condition' will become a 'yellow condition' or a 'red condition', or a 'flashing red condition', each of which in turn calls for, first and foremost, the patient's attention and engagement in corrective action, and an echoing attention and engagement of the care giver(s) to assure that the best possible corrective actions are made by the patient. It is also desirable to use a more transparent term than 'cubic distance', e.g., Timing Error.

Preferred Embodiment: Antiretroviral Drug Treatment of HIV Infection

The Vrijens thesis describes the method for computing Timing Error (cubic distance), which appears to be the most robust predictor of the separate probabilities of improvement or deterioration in HIV-infected patients' clinical status. Timing Error (cubic distance) is derived from analysis of the variations in the electronically captured data on time-intervals between doses. One then computes the probabilities for improvement and for deterioration, which depend in a preferred embodiment having to do with infection with human immunodeficiency virus (HIV), on the present range of 'viral load', which is the number of virus particles per unit volume of blood plasma. The choice to use strata of viral load instead of absolute values provides a form of filtering that excludes small changes in measured viral load, deemed too small to be of clinical importance. Thus, a decrease from 5000 particles to 2500 particles, though large in absolute number has little clinical importance, in and of itself, whereas a decrease from 200 to less than 50 has substantial clinical importance. In particular the strata of compliance needed to drive viral load to or below its lowest detectable level are much more stringent, than to drive a high viral load downward by a numerically much greater reduction than needed for the penultimate steps in viral load reduction.

The compliance-dependent probabilities of (i) substantive improvement in the patient's health status, and (ii) substantive deterioration in the patient's health status which are determined by the method of the present invention, are specific to particular drugs and patient health status. These probabilities can be calculated for different drugs and will reflect the different degrees of forgiveness of the drug regimen.

System for Implementing

The methods of the present invention described above may be implemented with a system for medication monitoring which includes software for analyzing data and determining probabilities and a medication dispenser for monitoring dosing and warning of non-compliance. A computer-readable medium or software according to one embodiment contains executable code for analyzing data on the clinical consequences of variable patient compliance with a prescribed drug regimen to determine the compliance-dependent probabilities of (i) substantive improvement in the patient's health status, and (ii) substantive deterioration in the patient's health status. The patient or caregiver enters data about the patient's health status and drug regimen to be prescribed into the computer which in turn communicates the compliance-dependent probabilities to the caregiver and patient as easily interpreted data indicating probability of improvement and probability of deterioration. The medication dispenser which is provided to the patient includes a recorder or means for recording dosing events and their time and date of occurrence, plus a warning system for warning the patient of non-compliance with an intensity and urgency based on defined acceptable levels of probabilities which have been determined by the patient and caregiver.

Applicability to Other Chronic Diseases Besides HIV Infection

The basic approach of computing 'cubic distance' or Timing Error variations in interdose intervals is applicable to other diseases, e.g., arterial hypertension or adult-onset diabetes mellitus, by following the principles and procedures described herein for the preferred embodiment, namely: to define ranges of the controlled variables, e.g., systolic blood pressure and diastolic blood pressure in the case of hypertension, and the concentration of glucose in blood in the case of diabetes mellitus. One could optimally allow the exponent in the computation of cubic distance or Timing Error to vary, to find the exponent that gives the model the greatest explanatory power. It seems likely, however, that a value in the vicinity of 3 will be optimal in most situations, but would be closer to 2 for a relatively unforgiving, short-acting drug whose therapeutic effects are interrupted by short lapses in dosing.

Although the computation of the 'cubic distance' or Timing Error is the preferred method for assigning relative weights to lapses in dosing for the HIV example, other methods of analyzing the lapses in dosing may be more appropriate for other drugs or diseases.

Conclusion

As is well-known to those skilled in the art of risk communication, the estimations of risk usually depend upon complex, model-based, statistical maneuvers, which are understood only by those few who are knowledgeable in such matters. The results of such computations, however, can, and should, be presented in the simplest possible terms, which is subsumed within the art of risk communication. In the present matter, the computations described by Vrijens, with his innovative recognition of the separate probabilities for improvement and for deterioration, lay the foundation for a simple, color-coded management system that intervenes, based on ongoing compliance data, in the manner described by Urquhart (9) and by Urquhart and Elgie (10) to take corrective actions contingent upon the dosing history. What is also novel here is the ability to set probability levels for preventing deterioration and for achieving improvement, and to forecast the future costs, in professionals' time, in the patient's time, and in monetary terms, of acting on those choices.

EXAMPLE

According to one example, the method of medication monitoring according to the present invention can be used for patient empowerment and improved treatment and may follow the following exemplary scenario. The patient and caregiver monitor the patients' compliance with a prescribed drug regimen, such as with a medication dispenser and recorder. The patient and caregiver then discuss the past dosing history and with the help of a computer program analyze variations in patient compliance with the prescribed drug regimen to determine the probabilities of substantive improvement in the patient's health and substantive deterioration in the patient's health status calculated as described above. The patient and caregiver may then negotiate acceptable probabilities of respective improvement and deterioration and translate these defined acceptable levels of probabilities into color coded warnings of green, yellow, red, and flashing red warnings. The patient and caregiver may then wish to review the color coded warning levels set to determine if these warning levels will be overly obtrusive for the patient's lifestyle. For example, if the acceptable probabilities negotiated require that the warning system warn the patient every time a dose is late by less than one hour, the patient may be easily aggravated by the warning system and tempted to ignore or abandon the warning system. Accordingly, after a review or after a trial period, the patient and caregiver may wish to renegotiate acceptable levels of the probabilities of improvement and deterioration to set more patient compatible warning levels. In addition, the warning system may be relaxed in special circumstances, such as on special occasions or during travel, to have less interference with the patient's lifestyle while still obtaining the desired result. The warning system may also be accelerated under some circumstances, such as in preparation for travel or upon return from travel.

While the invention has been described in detail with reference to the preferred embodiments thereof, it will be apparent to one skilled in the art that various changes and modifications can be made and equivalents employed, without departing from the present invention.

What is claimed is:

1. A method of medication monitoring comprising:
   analyzing data on the clinical consequences of variable patient compliance with a prescribed drug regimen to determine the compliance-dependent probabilities of (i) substantive improvement in the patient's health status, and (ii) substantive deterioration in the patient's health status;
   communicating the compliance-dependent probabilities to caregivers and patients;

defining acceptable levels of the probabilities of improvement and deterioration;

prescribing a drug regimen for the patient;

measuring patient compliance with the prescribed drug regimen with a medication dispenser having a recorder for recording dosing events; and intervening with the patient to improve compliance with an intensity and urgency based on the defined acceptable levels of probabilities.

2. The method of claim 1, wherein the analysis of data on the clinical consequences of variable patient compliance involves the calculation of cubic distance or Timing Error from the variations in intervals between dosages, and which has explanatory power for clinical outcomes superior to that provided by other parameters derived from patients' dosing histories.

3. The method of claim 1, wherein step of intervening involves warning the patient with a graduating warning system including different colored lights on the medication dispenser.

4. The method of claim 1, wherein the step of intervening involves warning the patient by a remote warning center after communication between the remote warning center and electronics associated with the medication dispenser.

5. The method of claim 1, wherein substantive improvement and deterioration in the patient's health status occurs when a measurement of a patient's health indicator changes between predetermined levels of the health indicator.

6. The method of claim 5, wherein the patient's health indicator is the viral load and the predetermined levels each include a range of viral loads.

7. A method of medication monitoring comprising the steps of:

identifying a patient with a condition treatable with a prescribed drug regimen;

prescribing a drug regimen for the patient;

defining an acceptable level of compliance with the prescribed drug regimen, based on an analysis of clinical compliance data involving the calculation of a parameter, cubic distance or Timing Error, from the variations in intervals between dosages;

monitoring compliance of the patient with the prescribed drug regimen with a medication dispenser having a recorder for recording dosing events; and warning the patient with a graduated warning system that is based on the defined acceptable level of compliance.

8. The method of claim 7, wherein the patient is warned with a graduating warning system including differently colored lights on the medication dispenser.

9. The method of claim 7, wherein the patient is warned by a remote warning center after communication between the remote warning center and electronics associated with the medication dispenser.

10. The method of claim 7, wherein the step of defining an acceptable level of compliance involves accessing the clinical compliance data for the particular drug regimen, wherein the clinical compliance data includes both a probability of improvement in patient health and a probability of deterioration in patient health.

11. The method of claim 7, wherein the step of defining an acceptable level of compliance involves accessing the clinical compliance data for the particular drug regimen, wherein the clinical compliance data is broken down into categories based on patient health status.

12. The method of claim 7, comprising a step of compiling a drug dosing history from the recorded dosing events and reviewing the defined acceptable level of compliance based on the drug dosing history.

13. A method of medication monitoring comprising:

analyzing data on the clinical consequences of variable patient compliance with a prescribed drug regimen to determine the compliance-dependent probabilities of (i) substantive improvement in the patient's health status, and (ii) substantive deterioration in the patient's health status;

defining patient acceptable levels of the probabilities of improvement and deterioration;

measuring patient compliance with the prescribed drug regimen with a medication dispenser having a recorder for recording dosing events; and intervening with the patient to improve compliance when the defined acceptable levels of probabilities are exceeded.

14. The method of claim 13, wherein the analysis of data on the clinical consequences of variable patient compliance involves the calculation of cubic distance or Timing Error from the variations in intervals between dosages, and which has explanatory power for clinical outcomes superior to that provided by other parameters derived from patients' dosing histories.

15. The method of claim 13, wherein step of intervening involves warning the patient with a graduating warning system including different colored lights on the medication dispenser.

16. The method of claim 13, wherein the step of intervening involves warning the patient by a remote warning center after communication between the remote warning center and electronics associated with the medication dispenser.

17. The method of claim 13, wherein substantive improvement and deterioration in the patient's health status occurs when a measurement of a patient's health indicator changes between predetermined levels of the health indicator.

18. The method of claim 17, wherein the patient's health indicator is the viral load and the predetermined levels each include a range of viral loads.

19. The method of claim 13, comprising a step of compiling a drug dosing history from the recorded dosing events and reviewing the defined acceptable level of compliance based on the drug dosing history.

20. A system for medication monitoring comprising:

a computer readable medium containing executable code for:

analyzing data on the clinical consequences of variable patient compliance with a prescribed drug regimen to determine the compliance-dependent probabilities of (i) substantive improvement in the patient's health status, and (ii) substantive deterioration in the patient's health status; and communicating the compliance-dependent probabilities to caregivers and patients; and a medication dispenser having a recorder for recording dosing events a warning system for warning the patient of non-compliance with an intensity and urgency based on defined acceptable levels of probabilities.

21. The system of claim 20, wherein the analysis of data on the clinical consequences of variable patient compliance involves calculation of cubic distance or Timing Error from the variations in intervals between dosages.

22. The system of claim 20, wherein the medication dispenser comprises a graduating warning system including different colored lights.

23. The method of claim 20, wherein the medication dispenser delivers a signal to a remote warning center.

* * * * *